United States Patent [19]
Lazzara et al.

[11] Patent Number: 5,695,336
[45] Date of Patent: Dec. 9, 1997

[54] DENTAL IMPLANT FIXTURE FOR ANCHORAGE IN CORTICAL BONE

[75] Inventors: Richard J. Lazzara; Keith D. Beaty, both of West Palm Beach, Fla.

[73] Assignee: Implant Innovations, Inc., Palm Beach Gardens, Fla.

[21] Appl. No.: 601,841

[22] Filed: Feb. 15, 1996

Related U.S. Application Data

[63] Continuation of Ser. No. 222,928, Apr. 5, 1994, abandoned, which is a continuation-in-part of Ser. No. 845,138, Mar. 3, 1992, Pat. No. 5,364,268.

[51] Int. Cl.⁶ ...................................................... A61C 8/00
[52] U.S. Cl. ........................................... 433/173; 433/174
[58] Field of Search ................................ 433/173, 174, 433/175, 176

[56] References Cited

U.S. PATENT DOCUMENTS

| | | |
|---|---|---|
| 2,112,007 | 3/1938 | Adams . |
| 3,067,740 | 12/1962 | Haboush . |
| 3,488,779 | 1/1970 | Christensen . |
| 3,846,846 | 11/1974 | Fischer . |
| 4,145,764 | 3/1979 | Suzuki et al. . |
| 4,414,966 | 11/1983 | Stednitz . |
| 4,424,037 | 1/1984 | Ogino et al. ............... 433/173 |
| 4,463,753 | 8/1984 | Gustilo . |
| 4,468,200 | 8/1984 | Münch ............... 433/174 |
| 4,480,997 | 11/1984 | Deutsch et al. ............... 433/221 |
| 4,484,570 | 11/1984 | Sutter et al. . |
| 4,495,664 | 1/1985 | Blanquaert . |
| 4,511,335 | 4/1985 | Tatum, Jr. ............... 433/173 |
| 4,535,487 | 8/1985 | Esper et al. ............... 623/22 |
| 4,537,185 | 8/1985 | Stednitz . |
| 4,668,191 | 5/1987 | Plischka ............... 433/174 |
| 4,713,003 | 12/1987 | Symington et al. ............... 433/173 |
| 4,713,004 | 12/1987 | Linkow et al. ............... 433/174 |
| 4,722,688 | 2/1988 | Lonca ............... 433/173 |
| 4,738,623 | 4/1988 | Driskell ............... 433/173 |
| 4,790,753 | 12/1988 | Fradera ............... 433/174 |
| 4,793,808 | 12/1988 | Kirsch ............... 433/173 |
| 4,826,434 | 5/1989 | Krueger ............... 433/174 |
| 4,851,008 | 7/1989 | Johnson ............... 623/16 |
| 4,854,872 | 8/1989 | Detsch ............... 433/173 |
| 4,863,383 | 9/1989 | Grafelman ............... 433/174 |

(List continued on next page.)

FOREIGN PATENT DOCUMENTS

| | | |
|---|---|---|
| 0 111134 | 6/1984 | European Pat. Off. . |
| 0 126624 | 11/1984 | European Pat. Off. . |
| 0 139052 | 5/1985 | European Pat. Off. . |
| 0216031 | 4/1987 | European Pat. Off. . |
| 0237505 | 9/1987 | European Pat. Off. . |
| 0 288702 | 11/1988 | European Pat. Off. . |
| 0 530160 | 3/1993 | European Pat. Off. . |
| 3043336 | 11/1981 | Germany . |
| 332486 | 2/1971 | Sweden . |
| 1 291 470 | 10/1972 | United Kingdom . |

OTHER PUBLICATIONS

Langer et al., "The Wide Fixture: A Solution for Special Bone Situations and a Rescue for the Compromised Implant. Part 1," The International Journal of Oral & Maxillofacial Implants, pp. 400–408, vol. 8, No. 4, 1993 (9 pages).

(List continued on next page.)

*Primary Examiner*—Cary E. O'Connor

[57] ABSTRACT

A dental implant fixture intended for installation in maxillary and mandibular posterior regions where bone is cancellous internally and cortical externally characterized by buccal and lingual cortical plates bounding a relatively large body of cancellous bone. The body of the implant fixture has a width dimension that is substantially the same as the distance between the buccal and lingual cortical plates in the site of installation and has a stop flange of substantially the same width at its gingival end. When the implant is installed in that site the stop flange makes bone-to-implant contact with the coronal bone which joins the plates. The length of this implant fixture is limited so that when so installed it does not make contact with the mandibular canal or the sinus cavity.

59 Claims, 4 Drawing Sheets

U.S. PATENT DOCUMENTS

| | | | |
|---|---|---|---|
| 4,878,915 | 11/1989 | Brantigan | 623/17 |
| 4,915,628 | 4/1990 | Linkow et al. | 433/173 |
| 4,932,868 | 6/1990 | Linkow et al. | 433/174 |
| 4,934,935 | 6/1990 | Edwards | 433/174 |
| 4,960,381 | 10/1990 | Niznick | 433/174 |
| 4,978,350 | 12/1990 | Wagenknecht | 606/72 |
| 4,988,299 | 1/1991 | Branemark | 433/174 |
| 5,015,186 | 5/1991 | Detsch | 433/173 |
| 5,026,280 | 6/1991 | Dürr et al. | 433/173 |
| 5,049,073 | 9/1991 | Lauks | 433/173 |
| 5,061,181 | 10/1991 | Niznick | 433/174 |
| 5,064,425 | 11/1991 | Brånamark et al. | 606/72 |
| 5,076,788 | 12/1991 | Niznick | 433/173 |
| 5,078,607 | 1/1992 | Niznick | 433/174 |
| 5,100,323 | 3/1992 | Friedman et al. | 433/174 |
| 5,188,800 | 2/1993 | Green, Jr. et al. | 422/23 |
| 5,205,745 | 4/1993 | Kamiya et al. | 433/174 |
| 5,209,659 | 5/1993 | Friedman et al. | 433/173 |
| 5,254,005 | 10/1993 | Zuest | 433/173 |
| 5,269,685 | 12/1993 | Jörnéus et al. | 433/174 |
| 5,312,256 | 5/1994 | Scortecci | 433/173 |
| 5,324,199 | 6/1994 | Branemark | 433/174 |
| 5,435,723 | 7/1995 | O'Brien | 433/174 |
| 5,449,291 | 9/1995 | Lueschen et al. | 433/173 |
| 5,591,029 | 1/1997 | Zuest | 433/174 |

OTHER PUBLICATIONS

Academy of Osseointegration Program, Mar. 4–6, 1993, cover page and pp. 32–33.

Bone Screw Technical Information by Richards Technical Publication (1980, pp. 1–14).

Sustain®, H–A Bointegrated Dental Implant System, 1991.

Steri–Oss, The Future of Implant Dentistry, 1990.

OsteoImplant Corp., 1990.

Southern Implants, B–Series Dental Implants, Apr. 1, 1993.

Interpore, Price and Data Sheet, 1989.

Imtec, Hexed Head Implant Systems, Spring 1993 Catalog, 1993.

Implant Support Systems, Inc., Products for diagnosis, surgery, restoration, laboratory, 1989.

Implamed, The Source, Nov. 1992.

Dentsply, Restorative Manual, 1992.

Dentsply, Price List Jun. 1, 1992.

"Titanodont™ Subcortical Implant System," Miter, Inc.

"Ha–Ti Implant Short Neck Measuring Template," Mathys Dental LTD, Aug. 1992.

Core–Vent Corporation "Spectra System: The Only Complete System of Osseointegrated Implants", 1990.

Core–Vent Corporation "Diagnosis And Treatment Planning Guidelines", Oct. 12, 1989.

Core–Vent "Les Systemes Implantaires", Jan. 10, 1990.

"Cemented Abutments for Crown and Bridge", Date Prior to Filing Date.

Core–Vent Corporation "Order Form", Sep. 1989.

Core–Vent Corporation "The Longitudinal Clinical Efficacy of Core–Vent Dental Implants: A Five–year Study", Journal of Oral Implantology, vol. XV, No. 2, 1989.

Ledermann, Frischherz, and Markwalder, "The Ha–Ti Implant", Schweiz Monatsschr Zahnmed, vol. 101, May 1991.

Driskell Bioengineering, "The DB Precision Implant System 1000 Series", 1986.

U. Lekholm, "The Branemark Implant Technique: A Standardized Procedure Under Continuous Development," 2nd Int. Tissue International Congress, Rochester, Minnesota, Sep. 1990, pp. 194–199.

Jaffin & Berman "The Excessive Loss of Branemark Fixtures in Type IV Bone: A 5–Year Analysis," J. Peridontal, 1991, 62:2–4.

Langer, B. et al., "Osseointegration: Its Impact On the Interrelationship of Periodontics And Restorative Dentistry: Part 1," The International Journal of Periodontics & Restorative Dentistry, vol. 9, No. 2, 1989 at pp. 85 to 105.

DENTAL IMPLANT FIXTURE FOR ANCHORAGE IN CORTICAL BONE

This application is a file wrapper continuation of application Ser. No. 08/222,928, filed Apr. 5, 1994 now abandoned, which is a continuation-in-part of application Ser. No. 07/845,138 filed Mar. 3, 1992 and issued as U.S. Pat. No. 5,364,268.

BACKGROUND OF THE INVENTION

This invention relates to dental implant fixtures, particularly to fixtures intended for installation in the maxillary and mandibular posterior regions where bone is cancellous internally and cortical externally.

As it has developed to the present time, the technology of dental implant fixtures preferentially employs cylindrical implant fixtures, some externally threaded, and some not so threaded, but all being much longer than they are wide with the ratio of length to width being about 1.8 to 5.3, for example. This may be due primarily to the fact that early successes were experienced with installation in the anterior area of dental arches, using dental implant fixtures which have lengths ranging up to about 20 mm and widths up to about 4 mm. Predictability of this type of installation in the anterior area of dental arches is now so good that the use of dental implant fixtures has entered the armamentarium of oral surgeons, prosthodontists and periodontists in the treatment of fully and partially edentulous patients. Attempts to install dental implant fixtures in posterior regions of the maxillary and mandibular arches have, however, encountered several unique problems.

On the one hand, such attempts have been frustrated by the presence of the inferior alveolar nerve chamber (mandibular canal) in posterior mandible, and by the presence of the sinus cavities superior to the posterior maxillary bone crest. Risk of invading the sinus cavities and the mandibular canal is generally avoided, the result being that often in these posterior regions no more than about 8 mm or less of bone depth is available in which to prepare a bore to receive a dental implant fixture. Therefore, very short implants were placed with less square millimeters of surface area in bone for foundation. Lekholm reported reduced success with shorter implants. (2nd Int. Tissue International Congress, Rochester, Minn., September 1990). In order to place longer implant fixtures in these regions, many surgeons have resorted to more aggressive surgical techniques, including sinus lift procedures and mandibular nerve repositioning procedures. These procedures are obviously of greater risk than standard implant treatment in the anterior regions of the mouth. It is an advantage of the present invention to avoid these procedures. Some practitioners have sought to overcome this problem in the mandible, if the mandibular canal is located in a buccal position, by installing an available dental implant fixture closer to the lingual surface, and thereby bypassing the mandibular canal, when adequate bone is available to the lingual surface to avoid the risk of fenestration. This procedure, when available, may have the advantage of providing partial primary stabilization in cortical bone, which is important for eventual osseointegration of the fixture with the bone.

It has become apparent that wider jawbones (as in the posterior regions) usually have more trabeculation and often are without adequate amounts of density of bone in their marrow spaces to provide anchorage for dental implant fixtures. In the maxillary and mandibular posterior regions the bone is cancellous internally and cortical externally, a condition sometimes termed "eggshell". It has been found to be often almost impossible to securely immobilize a dental implant fixture in the marrow spaces of posterior jawbone regions. Jaffin & Berman noted less success in bone in posterior regions. J. Periodontal, 1991, 62:2–4. It has been suggested that the only hope of more predictable success in these cases is to place a dental implant fixture so as to engage a denser, more cortical layer of bone that often protects the maxillary and nasal sinuses, or that covers the mandibular canal, or engaging buccal-lingual plates in the posterior mandible or maxilla, all of which have inherent surgical risk.

The above-described difficulties and proposed solutions are presented in greater detail in an article by Langer, B. et al entitled "Osseointegration: Its impact on the Interrelationships of Periodontics and Restorative Dentistry: Part 1: The International Journal of Periodontics & Restorative Dentistry, Volume 9, Number 2, 1989, at pages 85 to 105.

GENERAL NATURE OF THE INVENTION

In accordance with the present invention a dental implant fixture having a cylindrically-shaped post portion which is preferably not more than about 13 mm long has a diameter preferably large enough (about 5 or 6 mm) to make bone-to-implant contact with cortical bone at both the lingual and buccal sides of posterior "eggshell" jawbone and includes stop means at its gingival end so that it can be installed without coming into contact with either the mandibular canal or the sinus floor. This new implant fixture has several advantages:

a—it has a length-to-width ratio in a range from about 0.833 to about 2.5 in dimensions providing bilateral bone-to-implant contact and a positive stop enabling installation without making contact with the mandibular canal or the sinus floor;

b—by contacting cortical bone at both sides of the bore in the jawbone and including a positive gingival stop at the superior cortex it provides more complete initial stabilization to the installed dental implant fixture; Langer et al., at page 89, show an installation in which a standard prior-existing long thin implant fixture is located to engage lingual cortical plate to provide initial stabilization, which obviously does not provide this advantage; the installation is in an unfavorable position for the construction of a fixed prosthesis;

c—owing to its larger width and gingival stop it provides a more stable platform for molar restorations than is available from the prior existing narrower implant fixtures, as well as larger surface area of an implant contact with bone, which results in smaller actual stresses in the bone-implant interface under a given occlusal load; these advantage are also lacking in Langer et al. Although the reaction of bone to stresses imposed by occlusal loading on implant fixtures is not well known and understood, it appears reasonable that any loading in the posterior regions of the mouth where cancellous bone is prevalent would benefit from a wider distribution of these stresses in the cortical bone.

d—non-circular (e.g.: hexagonal) manipulative and non-rotational devices now in use can be made wider to improve manipulation of the fixture and stabilization of restorations, especially single-tooth crowns, supported on them. In the existing state of the art of dental implants, the ratio of the width of the non-rotating feature to the total diameter of the implant is in a range of approximately 0.7 to 0.8. Maintaining this same ratio in a larger diameter implant (5 or 6 mm in diameter, for example) makes it possible to utilize a much larger dimension in the non-rotational features of the implant.

This larger dimension and positive gingival stop when used in conjunction with prosthetic components that have similar clearances or fit allowances between them as currently exist in the state of the art, provides for a much more stable interlocking mechanism. Essentially this revolves around the concept of retaining a minimum gap or fit between two components, but increasing the relative sizes of both of these components. By doing so, one allows the state of the art in existing manufacturing to be easily utilized to accomplish a more stable restoration when utilizing a larger diameter in the non-rotational dimensions of the components. By way of simple illustration, if one imagines a one-thousandth of an inch gap between an abutment and an implant fixture given the current state of the art, there will be a certain amount of play or micro movement between the prosthetic components and the implant fixture. If one can double the size of the non-rotational fitting, while still maintaining the same one- thousandth of an inch gap, the relative amount of motion or micro-movement between the prosthetic components and the implant fixture will decrease accordingly. The reduction of this relative motion is of significant advantage in keeping prosthetic components tight, particularly when used in single tooth applications.

In addition to the advantages offered by increased width of non- rotating fittings, the opportunity to increase the height or depth of such fittings may also offer significant advantages, particularly in single tooth restorations. The stability of the screw joint complex in single tooth restorations in the molar region is more important than in other regions of the mouth because of increased occlusal loads in this area. The addition of wider non-rotating features and taller or deeper non-rotating features, such as higher hexes or deeper hex sockets, will increase the integrity of the screw joint complex thereby reducing problems associated with micro movement and screw loosening.

e—Its larger size has advantages with regard to the final restoration and tooth emergence profile. Particularly in the posterior regions of the mouth where molars may be replaced, a larger diameter emergence profile may be desirable. This is particularly true in single tooth applications where it is important to preserve the emergence profile of a natural tooth in order to maintain subgingival contours which are easily cleaned and do not function as traps for debris and food. To create such tooth emergence profiles with smaller diameter implant fixtures often requires procedures such as ridge lapping or lingual bulking of restorative materials which makes hygiene very difficult. In anterior regions of the mouth it is often possible to overcome the shortcomings of narrower diameter implants by placing the implant more apically in the restored ridge. This allows for gradual contouring of the restoration subgingivally and can result in a more natural tooth emergence profile. However, in the posterior regions of the mouth this is often not practical because of limitations in anatomy which have been mentioned previously.

These and other advantages and features of the invention will become apparent from the following description of exemplary embodiments of the invention with reference to the accompanying drawings.

DETAILED DESCRIPTION OF THE DRAWINGS

Figure 1:
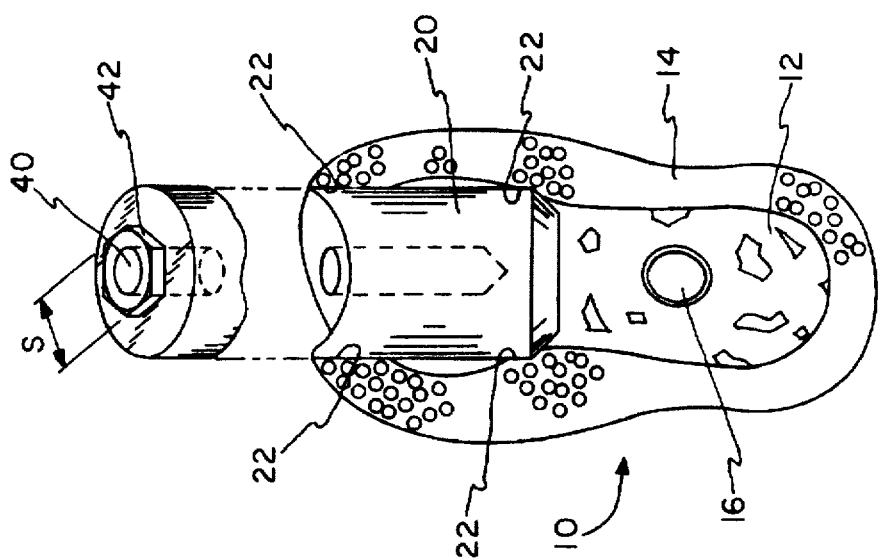
FIG. 1 is a schematic view of the cross-section of a mandibular posterior region with a dental implant fixture of the invention installed.

FIG. 1 schematically represents a posterior region 10 of a mandible, showing a typical eggshell configuration which is cancellous internally 12 and cortical externally 14. The mandibular canal 16 is in the cancellous portion of the mandible. A dental implant fixture 20 (shown more completely in FIG. 2) is installed in the mandible making full contact with coronal bone (superior cortex) and partial bone-to-implant contact with the lingual and buccal cortical walls 14 at locations labelled 22. Owing to the "egg-shell" condition existing in this region, the coronal opening into the jawbone is not countersunk, so as to maximize the area of the contact locations 22. For the most part, the implant fixture displaces cancellous bone 12. The coronal bone-to-implant contact, and lingual and buccal partial contacts 22 provide near-total initial stabilization to the implant at both the lingual and the buccal sides of the mandible.

Figure 2:
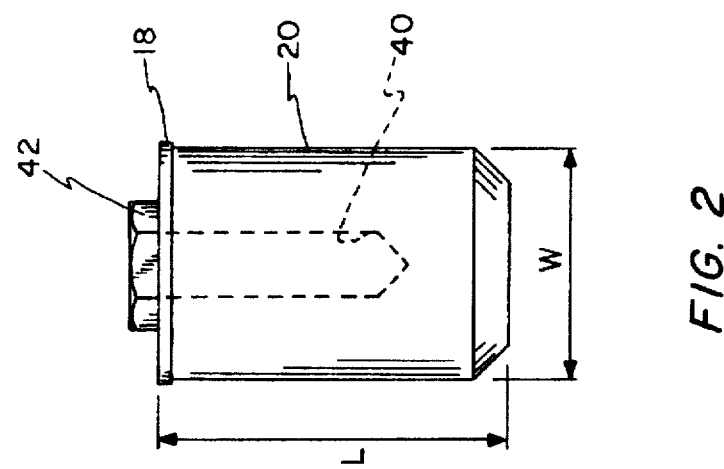
FIG. 2 illustrates schematically a dental implant fixtures according to the invention.

Referring now to FIG. 2, the implant fixture 20 of this invention is generally cylindrical in form, and has length L and width W dimensions which are unique and unlike the dimension of typical implant fixtures that are in regular current use. That width dimension W is not less than about 4.5 mm, and is preferably 5.0 mm to 6.0 mm. The ratio L/W is a range from about 0.833 to about 2.5. For example, L may be not more than about 8 to 13 mm, while W may be up to about 7 or 8 mm, depending on the width of the jawbone at the posterior location chosen for the implant fixture. The limit on L is dictated by the location of the mandibular canal 16, which may be less than 8 or 10 mm. In contrast to these unusual dimensions, implant fixtures currently available have lengths up to about 20 mm, and widths up to about 4 mm, thus having L/W ratios as high as 4.5, for example. A dental implant fixture having this LAN ratio and limited to L not greater than about 8 to 10 mm would not be able to make bone-to-implant contact with both sides of the cortical shell in a posterior location. According to the invention, the dental implant 20 has a top flange 18 that is not substantially wider than the fixture 20, and has a thin axial dimension, like the top flange 24 that is shown in and described in greater detail with reference to FIGS. 4 and 5.

Figure 3:
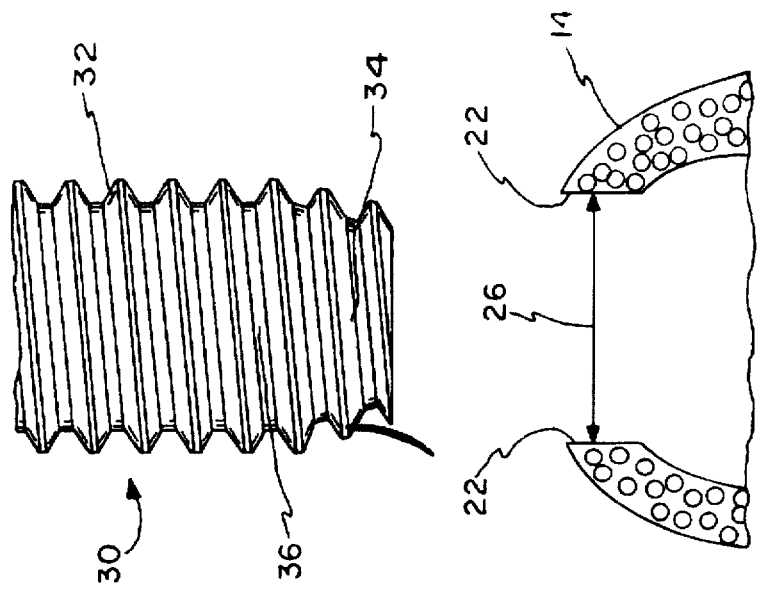
FIG. 3 is a partial side view of an externally-threaded dental implant fixture.

FIG. 3 shows schematically an implant fixture 30 bearing a screw thread 32 on its outer surface, for initial mechanical fixation of the implant fixture in the coronal wall and in the cortical walls 14. In accordance with this embodiment the lower or apical portion 34 of the implant body 36 may be tapered to a smaller diameter than the major portion of the implant body; both the peaks of the thread 32 and the roots of the threads taper substantially equally with the major and minor diameters parallel to each other. This feature may be used to thread an implant fixture into the opening 26 through the superior cortex in the cortical bone 14, where the contact locations 22 are not countersunk, for the reason explained above.

Figure 4A:
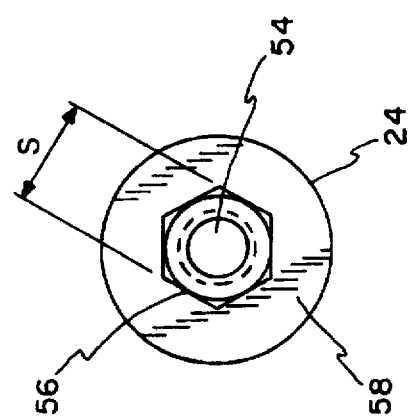
FIG. 4A is a top view of FIG. 4.
Figure 4:
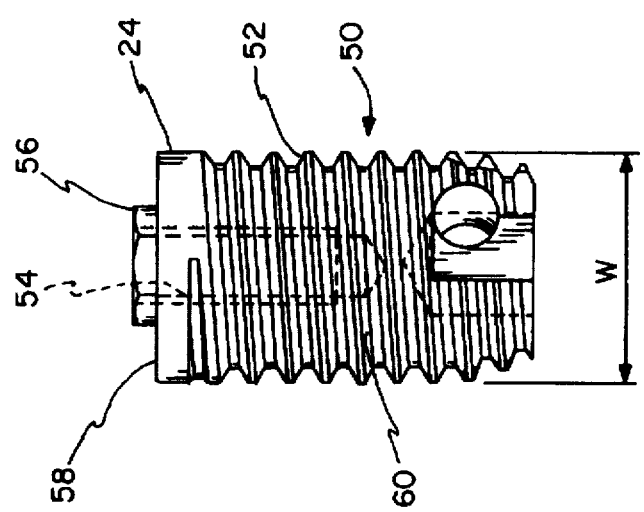
FIG. 4 is a slightly enlarged side view of an externally-threaded fixture in a form in which it may be manufactured.

FIGS. 4 and 4A show a cylindrical implant fixture 50 bearing an exterior screw thread 52 on a cylindrical body 60 of substantially uniform diameter W over its major portion (lengthwise), and tapered apically, like FIG. 3. A top flange 24 has substantially the same diameter as the peak diameter of the thread 52, and is itself without thread. The thickness of this flange 24 in the axial direction is limited to about 0.016 to about 0.020 mm up to about ¼ mm., preferably not more than about the root width of 1 to 2 adjacent turns of the thread 52. Its top to side edges are preferably sharp without burrs. This implant fixture has self-tapping features at its apical end. When it is threaded into the coronal opening 26 (see FIG. 3) the thread 52 engage coronal bone throughout the contact locations 22 and the top flange 24 is brought firmly to a stop just outside the coronal opening 26. The stop 24 may enter the coronal opening in part, where the thread ends, but should not displace the thread 52 in the opening 26.

Figure 5:
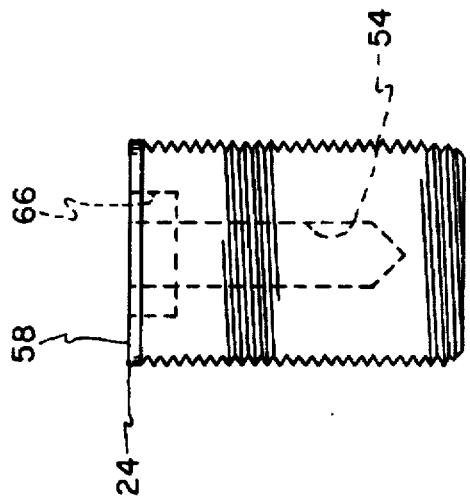
FIG. 5 is a side view of another dental implant fixture shown schematically.

In common with prior existing implant fixtures, the fixtures of this invention may have a receiving bore (40 in FIGS. 2 & 3; 54 in FIGS. 4 & 4A) for receiving and holding restoration components (not shown). This bore may be internally threaded as shown at 54 in FIG. 4. A non-circular (e.g: hexagonal) fitting 42 (FIG. 2), 56 (on top surface 58 of the flange 24 in FIG. 4) may be provided, externally as shown in these figures, or internally 66 as shown in FIG. 5, for the known purposes of manipulating the implant fixture and for stabilizing a restoration component against rotation with respect to the implant fixture around their common axis. The distance S between two opposite flat surfaces of this fitting may, however, be larger in the present invention than in the prior known implant fixtures, and the ratio between the width W and the dimension S can be selected to provide enhanced stabilization to the restoration components and to the restoration built on them, as is explained above in this specification.

Thus, for example, S can be greater than the usual 3 mm, while W can be up to about 10 mm. A dimension of S at 4 mm is closer to the diameter of a posterior tooth, and therefore more stabilizing. This yields a ratio of W/S that is about 2.5. If S is still larger, this ratio becomes smaller.

In use the externally-threaded implant fixtures of the present invention are installed in thread-engaging contact with at least the coronal bone, and preferably with both cortical walls 14, and the thin stop flange 24 engages the outer surface of the coronal bone to prevent insertion of the implant fixture beneath the superior cortex and possible contact with the mandibular canal. Countersinking of the coronal bone is not necessary, and should be avoided.

Wide diameter dental implants according to the invention provide an advantage in regenerative procedures. In the sinus graft area the larger diameter implant in the sinus graft reduces the amount of graft material which is necessary in order to fill the sinus for regeneration. In addition, in the extraction site, the large diameter implant fills the socket more and therefore requires less regeneration within the socket. Bone cells moving from the bone marrow have less distance to travel to reach the implant surface to regenerate bone and new osseointegrated surface.

Figure 8:
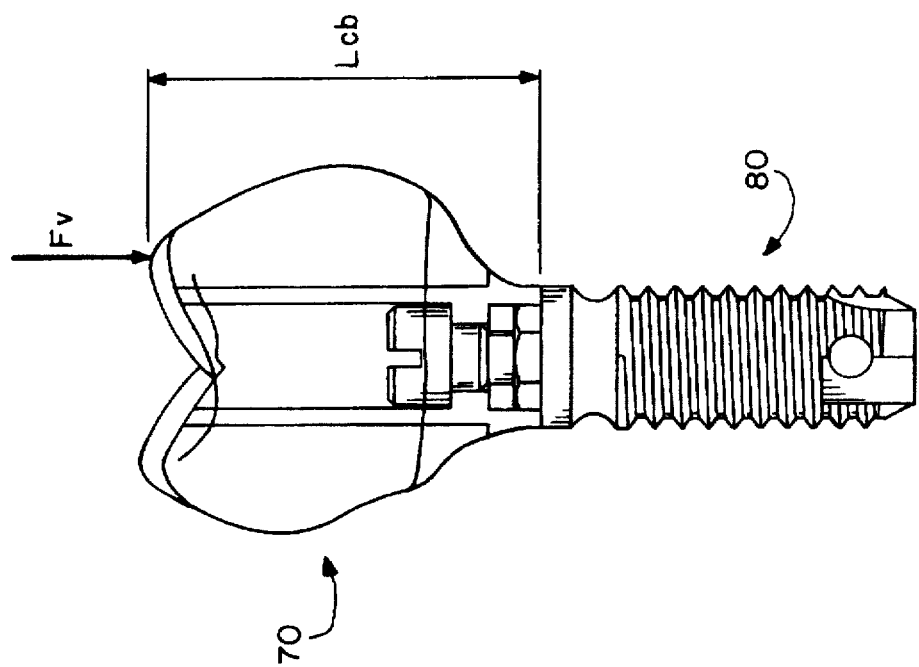
FIG. 8 illustrates the destructive dynamic forces imposed by the prior art.

Prosthetically, the unique design of the wide diameter dental implant according to the invention allows the support for the prosthesis to be brought out under the cusps of the teeth. This provides increased resistance to tipping forces and reduces stress on the abutment screw. Coordinated impression coping (not shown) can transfer the wider (e.g: 5 or 6 mm) dimension to the laboratory model so that a good emergence profile is developed and the support extends out substantially under the cusps of the teeth. Since maxillary and mandibular first molar teeth have approximately 6 mm from cusp tip to cusp tip buccal-lingually, a large diameter dental implant according to the invention will better withstand the occlusal loading since the shoulder of the implant comes out under those cusps tips. In the anterior bicuspid regions large diameter implants also provide better stability for these teeth, as well as developing better emergence profile. These advantages are illustrated in FIGS. 6, 7 and 8 of the drawings.

Figure 6:
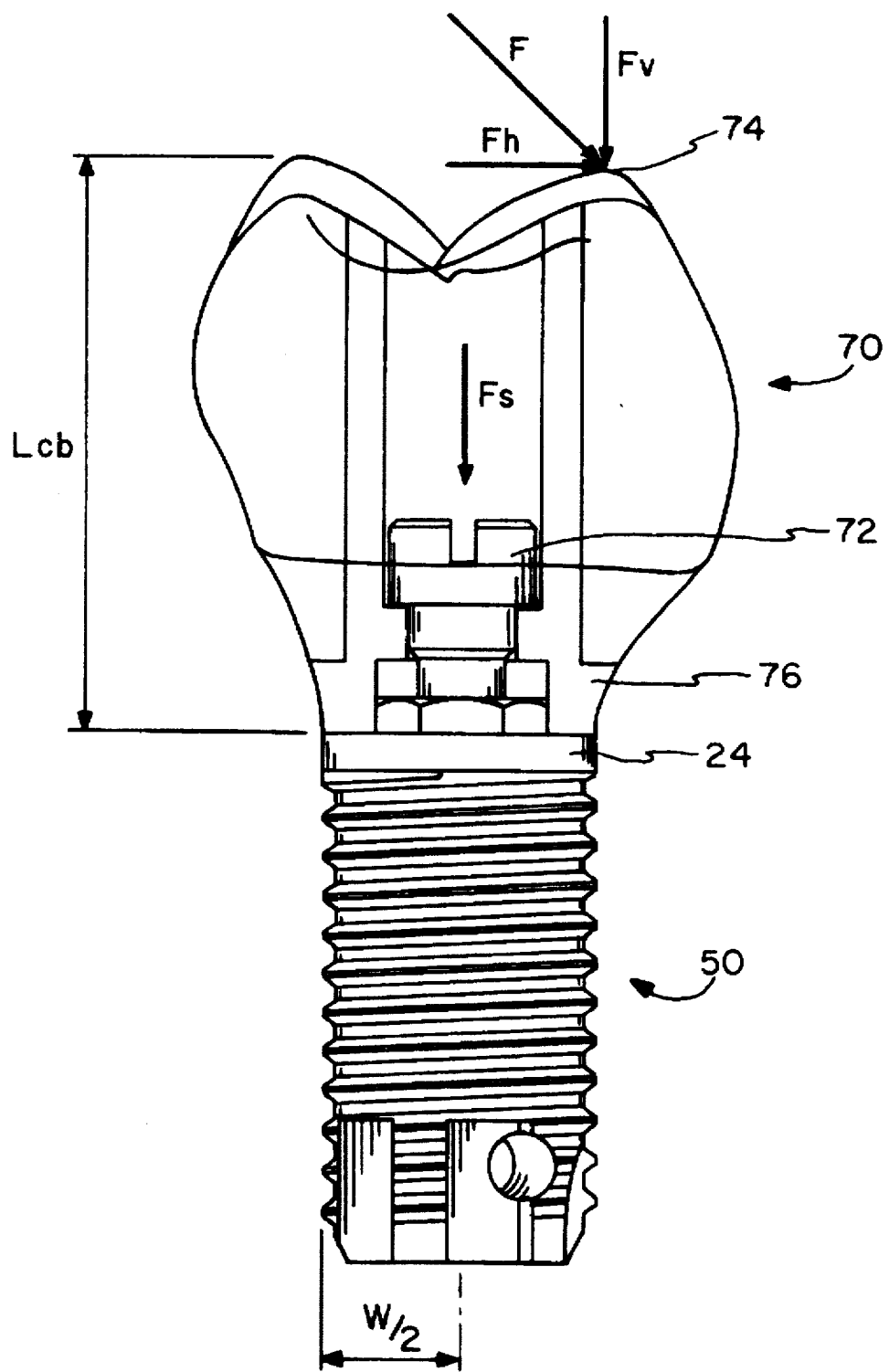
FIG. 6 shows an artificial tooth affixed to a dental implant.
Figure 7:
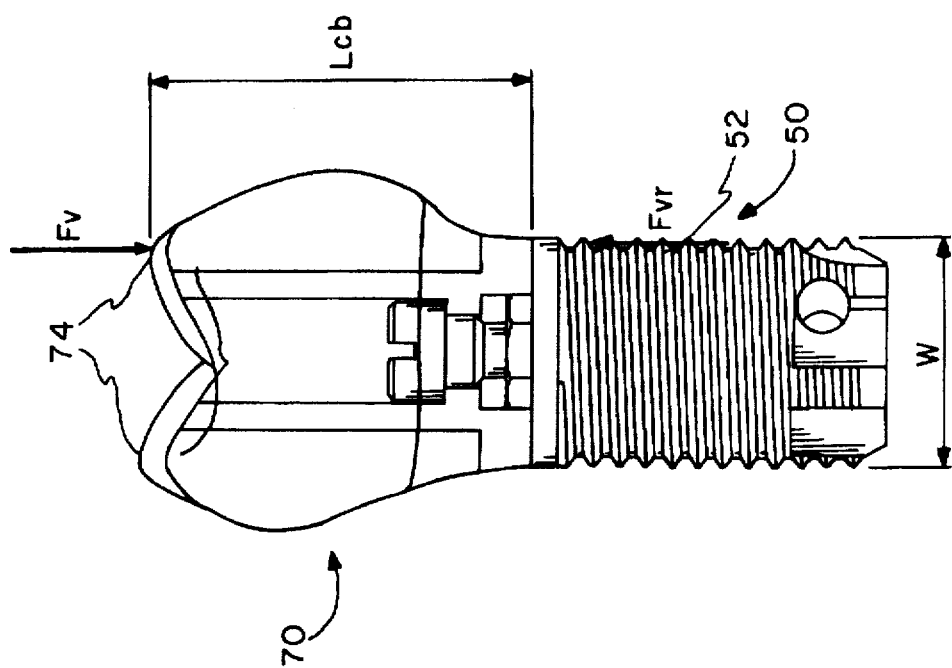
FIG. 7 is like FIG. 6, marked to illustrate improved dynamic forces made possible by the invention.

FIG. 6 shows an artificial tooth 70 of known form affixed to the dental implant 50 by means of an abutment screw 72 that is under a prescribed static installed tension. According to the invention, the abutment 76 on which the tooth 70 is formed has a wide base having a meeting surface in contract with top flange 18 or 24 and of substantially the same shape and diameter as the flange 18 or 24 and the implant 20 or 50, respectively. An analysis of the forces generated on the abutment screw due to mastication, for example, finds that a dental restoration made on the wide implant of the present invention benefits significantly relative to a similar restoration made on the narrower implants of the prior art.

In FIG. 6:

F=occlusal force on the tooth 70 applied at an angle which is generally normal to the surface of a cusp 74

Fv=vertical components of the occlusal force

Fh=horizontal or lateral component of the occlusal force

Fs=incremental tension in the abutment screw 72 resulting from Fh

Lcb=length of crown plus its abutment

W/2=one-half the diameter of the implant 50

The incremental tension Fs on the abutment screw 72 relative to the horizontal load Fh is defined in the relation:

$$Fh \times Lcb = Fs \times W/2$$

from which:

$$Fs = \frac{Fh \times Lcb}{W/2}$$

Thus, as W/2 becomes larger Fs becomes smaller. A dental restoration according to the present invention using wide implants and wide-base abutments with matching diameters of 5.00 mm or larger will put smaller incremental tension on the abutment screw 72 than would restorations made according to the prior art, given the same or similar horizontal load on the tooth. This improvement is illustrated with the aid of FIGS. 7 and 8.

In FIG. 7 the vertical component of force, Fv, bearing on cusp 74, generates a reactionary force component Fvr directly below it, substantially at or within the threads 52, at the boundary between the implant fixture and the host bone 14 (not shown in FIG. 7). There is little or no incremental tension Fs developed, and little or no tendency to twist the implant fixture in the bone.

In FIG. 8, on the other hand, where a prior art form of narrow implant fixture 80 is shown, W/2 is smaller, and the vertical component of occlusal force Fv, in a normal molar is outside the diameter of the implant fixture. This condition tends to produce greater incremental tension Fs as explained above, and it tends further to rock the implant fixture from side-to-side in its socket in the host bone. This risk is not acceptable in posterior locations, for reasons fully developed above.

We claim:

1. A dental implant fixture designed and intended for installation in a posterior jawbone region that is cancellous internally and cortical externally characterized by lingual and buccal cortical plates joined by superior cortical bone and bounding a relatively large body of cancellous bone occupying a substantial portion of the buccal-to-lingual thickness of said jawbone in said region, said fixture comprising:

an implant body having a gingival end, an apical end, a length dimension L and a width dimension W that is at least about 5.0 mm and substantially constant along a substantial portion of said length dimension L, said implant body having an external thread making multiple turns substantially along said length dimension L and suitable for effecting thread-engaging bone-to-implant contact between said implant and at least said superior cortical bone joining said plates when said implant fixture is installed through said superior cortical bone in said site with said gingival end near said superior cortical bone and said apical end penetrating said cancellous bone between said buccal and lingual cortical plates; and a stop flange having a maximum diameter which is not substantially larger than a peak-to-peak diameter of said external thread on said body, said stop flange limiting the penetration of said apical end into said jawbone.

2. An implant fixture according to claim 1 in which said flange is not threaded.

3. An implant fixture according to claim 1 in which an axial thickness of said flange is not substantially greater than the axial distance required for two adjacent turns of said external thread on said body.

4. An implant fixture according to claim 3 in which said flange is not threaded.

5. An implant fixture according to claim 1 in which said width dimension W is about 5.5 mm.

6. An implant fixture according to claim 1 in which said width dimension W is about 6.0 mm.

7. An implant fixture according to claim 1 in which said length dimension L is not more than about 13 mm.

8. An implant fixture according to claim 1 in which the length dimension L of said implant fixture exceeds said width dimension W by an amount that is not more than about 2.5 times said width dimension W.

9. An implant fixture according to claim 1 in which the ratio of the length dimension L of said implant fixture to said width dimension W is in a range from less than one-to-one to not substantially more than 2.5/1.0.

10. An implant fixture according to claim 1 in which said flange has a superior gingival surface that is substantially circular and a manipulating fitting is substantially centered on said gingival surface.

11. An implant fixture according to claim 10 in which the ratio of the diameter of said superior surface to the cross-sectional dimension of said fitting is not larger than about 2.5.

12. In combination a dental implant fixture according to claim 10 and an artificial tooth fixed to said dental implant fixture, said artificial tooth having a meeting surface in contact with said superior gingival surface, said meeting surface having substantially the same shape and size as said superior gingival surface.

13. A combination according to claim 12 in which said artificial tooth is fixed to said dental implant fixture with an abutment screw that is subjected to tension which is the sum of the installed static tension and an incremental increase due to lateral force imposed on said tooth, said width dimension W being effective to minimize said incremental increase.

14. A combination according to claim 12 in which the ratio of the diameter of said superior gingival surface to the cross-sectional dimension of said manipulating fitting is not larger than about 2.5.

15. An implant fixture according to claim 1 in which said body is tapered to a smaller diameter from a region near said apical end to said apical end of said body, and the peaks of said external thread are on a locus that is substantially equally tapered.

16. An implant fixture according to claim 15 in which said external thread extends between said apical end and said stop flange.

17. A dental implant fixture according to claim 1 in which the axial thickness of said stop flange is not greater than about one-quarter millimeter.

18. A dental implant fixture according to claim 17 in which said axial thickness of said stop flange is limited to about 0.016 to about 0.020 mm.

19. The dental implant of claim 1 which includes a manipulating fitting centered on a gingival surface of said stop flange, said gingival surface having a width that is at least twice the transverse width of said fitting.

20. An implant fixture according to claim 1 wherein said implant body has apical portion that tapers toward said apical end.

21. An artificial dental root fixture comprising a substantially cylindrical body made of a material that is biocompatible with living human jawbone, said body being unitary and having an outer surface, said body having an axial length that is not substantially greater than about 13 mm, a diametric width that is not substantially less than about 5 mm, and a thread on said outer surface making multiple turns around said body: and a stop flange having a maximum diameter not substantially larger than said diametric width of said body.

22. An artificial root according to claim 21 in which the axial thickness of said flange is not substantially greater than about the axial distance required for two adjacent turns of said thread on said body.

23. An artificial root according to claim 22 in which said flange has no threads.

24. In combination an artificial dental root fixture according to claim 21 and an artificial tooth fixed to said dental root fixture, said tooth having a meeting surface in contact with said stop flange, said meeting surface having substantially the same diameter as said stop flange.

25. A combination according to claim 24 in which said artificial tooth has on its occlusal surface one or more cusps each of which is substantially within said maximum diameter of said flange.

26. A combination according to claim 24 in which said artificial tooth is fixed to said dental root fixture with an abutment screw that is subjected to tension which is the sum of the installed static tension and an incremental increase due to lateral force imposed on said tooth, said diametric width being chosen to minimize said incremental increase.

27. A combination according to claim 24 in which the axial thickness of said stop flange is not greater than about one-quarter millimeter.

28. A combination according to claim 27 in which said axial thickness of said stop flange is limited to about 0.016 to about 0.020 mm.

29. A combination according to claim 24 wherein said body has apical portion that tapers toward said apical end.

30. An artificial dental tooth according to claim 21 in which the axial thickness of said stop flange is not greater than about one-quarter millimeter.

31. An artificial dental root according to claim 30 in which said axial thickness of said stop flange is limited to about 0.016 to about 0.020 mm.

32. An artificial root according to claim 21 wherein said body has apical portion that tapers toward said apical end.

33. A method of installing a dental implant fixture in a posterior region of a living human jawbone where said jawbone is cancellous internally and cortical externally and is characterized by lingual and buccal cortical plates joined by superior cortical bone and bounding a relatively large mass of cancellous bone occupying a substantial portion of the buccal-to-lingual thickness of said jawbone, comprising the steps of preparing a substantially cylindrical implant receiving bore penetrating the superior cortical bone without counter-sink in said jawbone at a selected site in said region, stopping said bore short of the mandibular canal or the maxillary sinus, as the case may be, selecting an implant fixture having a gingival end and an apical end, with stop means at the gingival end of said fixture having a diameter substantially the same as the diameter of said bore in said superior cortical bone for stopping substantially against the superior cortical bone when said fixture is installed in said bore, and a length L from said stop means not larger than the depth of said bore, and installing said fixture in said bore so as to make bone-to-fixture contact with at least said superior cortical bone and to bring said stop means into firm contact with said superior cortical bone, and thereby to effect initial stabilization of said implant fixture in said bore.

34. A method according to claim 33 including the step of preparing said bore to a diameter greater than 5 mm.

35. A method according to claim 33 including the step of preparing said bore to a depth greater than 5 mm but not greater than about 13 mm.

36. A method according to claim 33 including the step of preparing said bore to a diameter not greater than about 8 mm.

37. A method according to claim 33 including the step of preparing said bore to a diameter greater than about 5 mm, and a depth not greater than about 13 mm.

38. A method according to claim 33 in which said implant fixture is chosen to have a length-to-width ratio, L/W which is in a range from less than one-to-one to not more than about 2.5/1.0.

39. In combination, a dental implant fixture and an artificial tooth,
  said dental implant fixture having a gingival end and an apical end, said body being substantially cylindrical between said apical and gingival ends and having a diameter being greater than about 4.5 mm, said gingival end having a gingival surface with substantially the same diameter as said body, and a flange with a width not substantially larger than said diameter for stopping said apical end short of the inferior alveolar mandibular canal if said implant fixture is inserted in the posterior mandible and short of the superior sinus cavity if said implant fixture is inserted in the posterior maxillary bone, and
  said artificial tooth mounted on said implant fixture, said tooth having in contact with said gingival surface a meeting surface of substantially the same size and shape as said gingival surface.

40. A combination according to claim 39 in which said tooth has on its occlusal surface at least one cusp which is substantially within said width of said flange.

41. A dental implant fixture designed and intended for installation in a posterior jawbone region that is cancellous internally and cortical extremity characterized by lingual and buccal cortical plates bounding a relatively large body of cancellous bone occupying a major portion of the buccal-to-lingual thickness of said jawbone in said region, said fixture comprising:
  a substantially cylindrical implant body having a gingival end, a distal end, an exterior surface and a width dimension between said ends that is at least about 5.0 mm, said gingival end having a substantially flat gingival surface that is approximately bounded within said exterior surface of said body, said width dimension of said body being substantially constant between said gingival end and said distal end; and
  bone-engaging stop means at said gingival end for fixing said fixture in crestal bone between said lingual and buccal cortical plates in said region, the length L of said implant fixture between said ends being limited to less than about 13.0 mm so as to stop said distal end short of the superior sinus cavity if said region is in the posterior maxillary bone crest when said implant fixture is installed in said region with said gingival surface approximately flush with the surface of said crestal bone.

42. A dental implant fixture according to claim 41 in which said stop means is a substantially cylindrical flange that includes said gingival surface and extends axially toward said distal end not more than about ¼ mm, the diameter of said flange being substantially the same as width dimension of said implant body.

43. A dental implant fixture according to claim 41 in which said width dimension of said body is about 5.5 mm.

44. A dental implant fixture according to claim 41 in which said width dimension of said body is about 6.0 mm.

45. A dental implant fixture designed and intended for installation in a posterior jawbone region that is cancellous internally and cortical externally characterized by lingual and buccal cortical plates joined by superior cortical bone and bounding a relatively large body of cancellous bone occupying a substantial portion of the buccal-to-lingual thickness of said jawbone in said region, said fixture comprising:
  an implant body having a thread, a gingival end, an apical end, and a width dimension W that is at least about 5.0 mm and substantially constant between said apical end and gingival end, said thread making multiple turns around said body and suitable for effecting bone-to-implant contact between said implant and at least the superior cortical bone joining said plates when said implant fixture is installed through said superior cortical bone in said site, a minimum axial distance between adjacent surfaces on at least a pair of successive turns of said thread being approximately no larger than the maximum axial thickness of said thread; and
  a stop flange having a diameter which is larger than a minor diameter of said thread for limiting the penetration of said implant into said jawbone.

46. An implant fixture according to claim 45 wherein said flange is not threaded.

47. An implant fixture according to claim 45 wherein the axial thickness of said stop flange is not substantially greater than the axial distance required for two adjacent turns of said thread on said body.

48. An implant fixture according to claim 45 wherein said body has a length dimension L that is less than about 13 mm.

49. An implant fixture according to claim 45 wherein said apical end includes a self-tapping region, said self-tapping region having a diameter less than said width dimension W.

50. An implant fixture according to claim 49 wherein said manipulating fixture has a width that is from about 70% to about 80% of said width dimension W.

51. An implant fixture according to claim 45 wherein said diameter of said flange is approximately the same as said width W.

52. An implant fixture according to claim 45 wherein said body has apical portion that tapers toward said apical end.

53. A method of installing a dental implant in a posterior region of a living human jawbone where said jawbone is cancellous internally and cortical externally and is characterized by lingual and buccal cortical plates bounding a relatively large mass of cancellous bone occupying a major portion of the buccal-to-lingual thickness of said jawbone, comprising the steps of:

preparing an implant-receiving bore in said jawbone at a selected site in said region, said bore having a diameter being large enough to allow an implant to reach both of said plates;

stopping said bore short of the mandibular canal or the maxillary sinus, as the case may be;

choosing an implant having a diameter W at least as large as the diameter of said bore and a length L not larger than the depth of said bore, said implant having stop means to limit the penetration of said implant into said mandibular canal or said maxillary sinus; and installing said implant in said bore so as to make bone-to-implant contact with each of said plates and thereby to effect initial stabilization of said implant in said bore.

54. A method according to claim 53 including the step of preparing said bore to a diameter greater than 5 mm.

55. A method according to claim 53 including the step of preparing said bore to a depth greater than 5 mm but not greater than 10 mm.

56. A method according to claim 53 including the step of preparing said bore to a diameter not greater than about 8 mm.

57. A method according to claim 53 including the step of preparing said bore to a diameter greater than about 5 mm and a depth not greater than 10 mm.

58. A method according to claim 53 in which said implant is chosen to have a length-to-width ratio, L/W which is in a range from less than one-to-one to not more than about two-to-one.

59. A method according to claim 53 wherein said implant has a manipulating fitting at a gingival end, said fitting being apparently 70% to approximately 80% of said diameter W, said diameter W being greater than about 4.5 mm.

* * * * *

Disclaimer 5,695,336 - Richard J. Lazzara; Keith D. Beaty, both of West Palm Beach, Fla. DENTAL IMPLANT FIXTURE FOR ANCHORAGE IN CORTICAL BONE. Patent dated Dec. 9, 1997. Disclaimer filed March 22, 1999, by the assignee, Implant Innovations, Inc.

Hereby enters this disclaimer to claims 1-59 of said patent.
*(Official Gazette,* May 18, 1999)